United States Patent [19]

Yamamoto

[11] Patent Number: 5,177,002
[45] Date of Patent: Jan. 5, 1993

[54] IN VITRO ENZYMATIC CONVERSION OF GLYCOSYLATED HUMAN VITAMIN D BINDING PROTEIN TO A POTENT MACROPHAGE ACTIVATING FACTOR

[75] Inventor: Nobuto Yamamoto, 1040 66th Ave., Philadelphia, Pa., 19126

[73] Assignee: Nobuto Yamamoto, Philadelphia, Pa.

[21] Appl. No.: 576,248

[22] Filed: Aug. 31, 1990

Related U.S. Application Data

[63] Continuation-in-part of Ser. No. 439,223, Nov. 20, 1989, abandoned.

[51] Int. Cl.$^5$ ............... C12P 21/02; A61K 37/04; C07K 3/08; C07K 9/00
[52] U.S. Cl. ................... 435/68.1; 514/8; 530/380; 530/395; 530/402
[58] Field of Search ............ 435/68.1; 514/8, 2; 530/350, 351, 380, 402, 829, 395; 424/85.1

[56] References Cited

PUBLICATIONS

J. Svasti et al., *Journal of Biological Chemistry* 253:4188–4194, Jun. 25, 1978.
H. Van Baelen et al., *Journal of Biological Chemistry* 253:6344–6345, Sep. 25, 1978.
Cooke et al., *J. Clin. Invest.* 76:2420, 1985.
Yang et al., *Proc. Natl. Acad. Sci.* 82:7994, 1985.
Yamamoto et al., *Cancer Res.* 47:2008, 1987.
Yamamoto et al., *Cancer. Immunol. Immunother.* 25:185, 1987.
Yamamoto et al., *Cancer Res.* 24:6044, 1988.
Ngwenya et al., *Abstracts of the Annual Meeting of the American Society of Microbiology*, Abstract E-72, p. 121 (1988).
Homma, *Abstracts of the Annual Meeting of the American Society of Microbiology*, Abstract E-74, p. 121 (1988).

*Primary Examiner*—Robert A. Wax
*Assistant Examiner*—Stephen Walsh
*Attorney, Agent, or Firm*—Seidel, Gonda, Lavorgna & Monaco

[57] ABSTRACT

A novel, potent macrophage activating factor is prepared in vitro by treating glycosylated human group-specific component, also known as human vitamin D-binding protein, with glycosidases. Group-specific component, which is isolated from retired blood by known procedures, is thus readily converted to a highly potent macrophage activating factor.

22 Claims, 4 Drawing Sheets

```
                                          10
Leu Glu Arg Gly Arg Asp Tyr Glu Lys Asn Lys Val Cys Lys Glu
                20                                          30
Phe Ser His Leu Gly Lys Glu Asp Phe Thr Ser Leu Ser Leu Val
                                 40
Leu Tyr Ser Arg Lys Phe Pro Ser Gly Thr Phe Glu Gln Val Ser
                50                                          60
Gln Leu Val Lys Glu Val Val Ser Leu Thr Glu Ala Cys Cys Ala
                                 70
Glu Gly Ala Asp Pro Asp Cys Tyr Asp Thr Arg Thr Ser Ala Leu
                80                                          90
Ser Ala Lys Ser Cys Glu Ser Asn Ser Pro Phe Pro Val His Pro
                                100
Gly Thr Ala Glu Cys Cys Thr Lys Glu Gly Leu Glu Arg Lys Leu
               110                                         120
Cys Met Ala Ala Leu Lys His Gln Pro Gln Glu Phe Pro Thr Tyr
                                130
Val Glu Pro Thr Asn Asp Glu Ile Cys Glu Ala Phe Arg Lys Asp
               140                                         150
Pro Lys Glu Tyr Ala Asn Gln Phe Met Trp Glu Tyr Ser Thr Asn
                                160
Tyr Glu Gln Ala Pro Leu Ser Leu Leu Val Ser Tyr Thr Lys Ser
               170                                         180
Tyr Leu Ser Met Val Gly Ser Cys Cys Thr Ser Ala Ser Pro Thr
                                190
Val Cys Phe Leu Lys Glu Arg Leu Gln Leu Lys His Leu Ser Leu
               200                                         210
Leu Thr Thr Leu Ser Asn Arg Val Cys Ser Gln Tyr Ala Ala Tyr
                                220
Gly Glu Lys Lys Ser Arg Leu Ser Asn Leu Ile Lys Leu Ala Gln
               230                                         240
Lys Val Pro Thr Ala Asp Leu Glu Asp Val Leu Pro Leu Ala Glu (Continued in Figure 1B)
```

FIGURE 1A (Continued from Figure 1A)

```
                                          250
Asp Ile Thr Asn Ile Leu Ser Lys Cys Cys Glu Ser Ala Ser Glu
                260                                     270
Asp Cys Met Ala Lys Glu Leu Pro Glu His Thr Val Lys Leu Cys
                                280
Asp Asn Leu Ser Thr Lys Asn Ser Lys Phe Glu Asp Cys Cys Gln
                290                                     300
Glu Lys Thr Ala Met Asp Val Phe Val Cys Thr Tyr Phe Met Pro
                                310
Ala Ala Gln Leu Pro Glu Leu Pro Asp Val Arg Leu Pro Thr Asn
                320                                     330
Lys Asp Val Cys Asp Pro Gly Asn Thr Lys Val Met Asp Lys Tyr
                                340
Thr Phe Glu Leu Ser Arg Arg Thr His Leu Pro Glu Val Phe Leu
                350                                     360
Ser Lys Val Leu Glu Pro Thr Leu Lys Ser Leu Gly Glu Cys Cys
                                370
Asp Val Glu Asp Ser Thr Thr Cys Phe Asn Ala Lys Gly Pro Leu
                380                                     390
Leu Lys Lys Glu Leu Ser Ser Phe Ile Asp Lys Gly Gln Glu Leu
                                400
Cys Ala Asp Tyr Ser Glu Asn Thr Phe Thr Glu Tyr Lys Lys Lys
                410                                     420
Leu Ala Glu Arg Leu Lys Ala Lys Leu Pro Glu Ala Thr Pro Thr
                                430
Glu Leu Ala Lys Leu Val Asn Lys Arg Ser Asp Phe Ala Ser Asn
                440                                     450
Cys Cys Ser Ile Asn Ser Pro Pro Leu Tyr Cys Asp Ser Glu Ile
                                458
Asp Ala Glu Leu Lys Asn Ile Leu
```

FIGURE 1B

```
                                        10
Leu Glu Arg Gly Arg Asp Tyr Glu Lys Asn Lys Val Cys Lys Glu
            20                                              30
Phe Ser His Leu Gly Lys Glu Asp Phe Thr Ser Leu Ser Leu Val
                    40
Leu Tyr Ser Arg Lys Phe Pro Ser Gly Thr Phe Glu Gln Val Ser
                            50                              60
Gln Leu Val Lys Glu Val Val Ser Leu Thr Glu Ala Cys Cys Ala
                                        70
Glu Gly Ala Asp Pro Asp Cys Tyr Asp Thr Arg Thr Ser Ala Leu
                    80                                      90
Ser Ala Lys Ser Cys Glu Ser Asn Ser Pro Phe Pro Val His Pro
                                    100
Gly Thr Ala Glu Cys Cys Thr Lys Glu Gly Leu Glu Arg Lys Leu
                110                                         120
Cys Met Ala Ala Leu Lys His Gln Pro Gln Glu Phe Pro Thr Tyr
                                    130
Val Glu Pro Thr Asn Asp Glu Ile Cys Glu Ala Phe Arg Lys Asp
                140                                         150
Pro Lys Glu Tyr Ala Asn Gln Phe Met Trp Glu Tyr Ser Thr Asn
                                    160
Tyr Gly Gln Ala Pro Leu Ser Leu Leu Val Ser Tyr Thr Lys Ser
                170                                         180
Tyr Leu Ser Met Val Gly Ser Cys Cys Thr Ser Ala Ser Pro Thr
                                    190
Val Cys Phe Leu Lys Glu Arg Leu Gln Leu Lys His Leu Ser Leu
                200                                         210
Leu Thr Thr Leu Ser Asn Arg Val Cys Ser Gln Tyr Ala Ala Tyr
                                    220
Gly Glu Lys Lys Ser Arg Leu Ser Asn Leu Ile Lys Leu Ala Gln
                230                                         240
Lys Val Pro Thr Ala Asp Leu Glu Asp Val Leu Pro Leu Ala Glu
```

(Continued in Figure 2B)

FIGURE 2A (Continued from Figure 2B)

```
                                    250
Asp Ile Thr Asn Ile Leu Ser Lys Cys Cys Glu Ser Ala Ser Glu
            260                                         270
Asp Cys Met Ala Lys Glu Leu Pro Glu His Thr Val Lys Leu Cys
                                280
Asp Asn Leu Ser Thr Lys Asn Ser Lys Phe Glu Asp Cys Cys Gln
            290                                         300
Glu Lys Thr Ala Met Asp Val Phe Val Cys Thr Tyr Phe Met Pro
                                310
Ala Ala Gln Leu Pro Glu Leu Pro Asp Val Glu Leu Pro Thr Asn
            320                                         330
Lys Asp Val Cys Asp Pro Gly Asn Thr Lys Val Met Asp Lys Tyr
                                340
Thr Phe Glu Leu Ser Arg Arg Thr His Leu Pro Glu Val Phe Leu
            350                                         360
Ser Lys Val Leu Glu Pro Thr Leu Lys Ser Leu Gly Glu Cys Cys
                                370
Asp Val Glu Asp Ser Thr Thr Cys Phe Asn Ala Lys Gly Pro Leu
            380                                         390
Leu Lys Lys Glu Leu Ser Ser Phe Ile Asp Lys Gly Gln Glu Leu
                                400
Cys Ala Asp Tyr Ser Glu Asn Thr Phe Thr Glu Tyr Lys Lys Lys
            410                                         420
Leu Ala Glu Arg Leu Lys Ala Lys Leu Pro Asp Ala Thr Pro Lys
                                430
Glu Leu Ala Lys Leu Val Asn Lys Arg Ser Asp Phe Ala Ser Asn
            440                                         450
Cys Cys Ser Ile Asn Ser Pro Pro Leu Tyr Cys Asp Ser Glu Ile
                                458
Asp Ala Glu Leu Lys Asn Ile Leu
```

FIGURE 2B

IN VITRO ENZYMATIC CONVERSION OF GLYCOSYLATED HUMAN VITAMIN D BINDING PORTEIN TO A POTENT MACROPHAGE ACTIVATING FACTOR

This is a continuation-in-part of copending application Ser. No. 439,223, filed Nov. 20, 1989 now abandoned.

FIELD OF THE INVENTION

The invention relates to macrophage activation, in particular to the in vitro production of a potent macrophage activating factor.

BACKGROUND OF THE INVENTION

A. Inflammatory Response Results in Activation of Macrophages

Microbial infections of various tissues cause inflammation which results in chemotaxis and activation of phagocytes. Inflamed tissues release lysophospholipids due to activation of phospholipase A. Inflamed cancerous tissues produce alkyl-lysophospholipids and alkylglycerols as well as lysophospholipids, because cancerous cells contain alkylphospholipids and monoalkyl-diacylglyercols. These lysophospholipids and alkylglycerols, degradation products of membranous lipids in the inflamed normal and cancerous tissues, are potent macrophage activating agents (Yamamoto et al., *Cancer Res.* 47:2008, 1987; Yamamoto et al., *Cancer Immunol. Immunother.* 25:185, 1987; Yamamoto et al., *Cancer Res.* 24:6044, 1988).

Administration of lysophospholipids (5–20 µg/mouse) and alkylglycerols (10–100 ng/mouse) to mice activates macrophages to phagocytize immunoglobulin G-coated sheep red blood cells. The macrophages phagocytize the target red blood cells via their receptors recognizing the Fc portion of the immunoglobulin G but not the C3b portion of the complement (Yamamoto et al., *Cancer Res.* 47:2008, 1987).

In vitro treatment of mouse peritoneal macrophages alone with lysophospholipids or alkylglycerols results in no enhanced ingestion activity (Yamamoto et al., *Cancer Res.* 48:6044, 1988). However, incubation of peritoneal cells (mixture of macrophages and B and T lymphocytes) with lysophospholipids or alkylglycerols for 2–3 hours produces markedly enhanced Fc-receptor-mediated phagocytic activity of macrophages (Yamamoto et al., *Cancer Res.* 47:2008, 1987; Yamamoto et al., *Cancer Res.* 48:6044, 1988).

Incubation of macrophages with lysophospholipid- or alkylglycerol-treated B and T lymphocytes in a medium containing 10% fetal calf serum developed a greatly enhanced phagocytic activity of macrophages (Yamamoto et al., *Cancer Res.* 48:6044, 1988). Analysis of macrophage activating signal transmission among the nonadherent (B and T) lymphocytes has revealed that lysophospholipid- or alkylglycerol-treated B-cells can transmit a signalling factor to T-cells; in turn, the T-cells modify the factor to yield a new factor, which is capable of the ultimate stimulation of macrophages for ingestion capability (Yamamoto et al., *Cancer Res.* 48:6044, 1988).

B. Human Vitamin D-Binding Protein

The human vitamin D-binding protein, also known as "group-specific component" or "Gc protein", is an evolutionary conserved glycoprotein. It is a genetically polymorphic plasma protein having a relative molecular weight of about 52,000, normally constituting about 0.5% of the plasma proteins in man. The plasma concentration is generally about 260 µg/ml. Polymorphism of the Gc protein is demonstrable by gel electrophoretic analysis, which reveals two major phenotypes: Gc1 and Gc2 (Hirschfeld et al., *Nature* 185:931, 1960). The entire nucleotide coding sequences of the Gc1 and Gc2 genes, and the predicted amino acid sequences, have been reported (Cooke, et al., *J. Clin. Invest.* 76:2420, 1985; Yang et al., *Proc. Natl. Acad. Sci. USA* 82:7994, 1985). Gc1 is further divided into Gc1f and Gc1s subtypes which migrate electrophoretically as two bands, "fast" and "slow", because of a post-translational event involving sialic acid (Svasti et al., *Biochem.* 18:1611, 1979).

Coopenhaver et al., *Arch. Biochem. Biophys.* 226, 218–223 (1983) reported that the post-translational glycosylation difference occurs at a threonine residue, which appeared in a region of the protein having an amino acid difference between Gc1 and Gc2. While a CNBr fragment of Gc1 was found to contain N-acetylgalactosamine, no detectable galactosamine was reported in the homologous Gc2 CNBr fragment according to the method and criteria used. The Gc1 CNBr fragment further contained sialic acid, which was missing from the homologous region of Gc2.

Viau et al., *Biochem. Biophys. Res. Commun.* 117, 324–331 (1983), reported a predicted structure for the O-glucosidically linked glycan of Gc1, containing a linear arrangement of sialic acid, galactose and N-acetylgalactosamine linked to a serine or threonine residue.

The Gc protein may be purified by a variety of means, which have been reported in the literature. For example, the Gc protein may be purified by 25-hydroxy-vitamin $D_3$-Sepharose ® affinity chromatography from retired blood of the American Red Cross (Link, et al., *Anal. Biochem.* 157:262, 1986). The Gc protein can also be purified by actin-agarose affinity chromatography due to its specific binding capacity to actin (Haddad et al., *Bioch J.* 218:805, 1984).

Despite the characterization and intensive study of the human vitamin D-binding protein, and the existence of ready methods for its purification, the enzymatic conversion of this protein to a potent macrophage activity factor has not been demonstrated until the present invention.

SUMMARY OF THE INVENTION

A process for the production of a potent macrophage activating factor is provided. Human vitamin D-binding protein, which is identical to group-specific component in human serum, is a precursor of the macrophage activating factor. Group-specific component is converted to the factor by the action of glycosidases of B and T cells.

According to a process for preparing macrophage activating factor, group-specific component is contacted in vitro (i) with β-galactosidase, or (ii) with β-galactosidase in combination with sialidase, α-mannosidase or a mixture thereof. A potent macrophage activating factor is obtained in large quantities According to one embodiment of the invention, group-specific component of phenotype Gc1, subtype Gc1f, is contacted with β-galactosidase and sialidase to provide the macrophage activating factor. According to another embodiment, group-specific component of phenotype Gc1, subtype Gc1s, is contacted with β-galactosidase and α-mannosidase. Preferably, group-specific component of phenotype Gc1, subtype Gc1s, is contacted with not only β-galactosidase and α-mannosidase, but also sialidase, to ensure the conversion of the Gc1s variant (hereinafter Gc1s*) which contains sialic acid in lieu of α-mannose. Gc1s*, like Gc1f, requires treatment with β-galactosidase and sialidase for conversion to macrophage activating factor. In yet another embodiment, group-specific component of phenotype Gc2 is contacted with β-galactosidase alone to form the macrophage activating factor. Preferably, the macrophage activating factor is prepared by contacting pooled group-specific components comprising a mixture of Gc1f, Gc1s (Gc1s*) and Gc2 with all three enzymes to obtain the macrophage activating factor.

The invention also relates to a macrophage activating factor prepared according to the above process or any embodiment thereof, and compositions comprising the macrophage activating factor in combination with a pharmaceutically acceptable carrier.

The invention further relates to a method for inducing macrophage activation in an individual in need thereof by administering to such an individual macrophage activating effective amount of the novel macrophage activating factor.

"Group-specific component" or "Gc protein" as used herein means the genetically polymorphic glycoprotein, also known as "vitamin D-binding protein", including all genetic variations thereof, such as Gc2, Gc1, and subtypes such as Gc1f, Gc1s and Gc1s*. The singular expression "group-specific component" or "Gc protein" is thus understood to encompass all such variants, unless stated otherwise.

By "macrophage activation" is meant the stimulation of macrophages to an increased level of phagocytic activity.

DESCRIPTION OF THE FIGURES

FIGS. 1A–1B, and 2A–2B contain the reported amino acid sequence of human group-specific component, phenotypes Gc1 and Gc2, respectively. The underlined amino acid residues at positions 152, 311, 416 and 420 differ between the two proteins.

DETAILED DESCRIPTION OF THE INVENTION

A serum factor, which has been identified as human group-specific component, is converted to a macrophage activating factor by the action of B and T cell glycosidases. Human group-specific component exists as a polypeptide having attached thereto specific oligosaccharide moieties, certain of which are readily removable by treatment with readily available glycosidases. These glycosidases are equivalent to the functions of B and T cells upon the Gc protein. Upon treatment with specific glycosidases, group-specific component is unexpectedly converted to a highly potent macrophage activating factor. Thus, efficient conversion of Gc protein to the macrophage activating factor is achieved in vitro, in the absence of intact B- and T-cells. The novel macrophage activating factor formed by the enzymatic treatment of Gc protein is substantially pure and of such high potency that administration to a host of even a trace amount (500 picogram/kg of body weight) results in greatly enhanced phagocytic macrophage activity. Since the enzymatic generation of the novel factor bypasses the functions of B-and T-cells in macrophage activation, it has utility as a therapeutic agent for inducing macrophage activation, particularly in individuals afflicted with immunodeficient diseases, cancer or other immunocompromising diseases characterized by impaired B- or T-cell function.

T-cell lymphokine macrophage activating factor, also known as γ-interferon, is generated by lymphokine-producing T-cells in small amounts, or is obtained by genetic engineering. The novel macrophage activating factor of the invention, on the other hand, may be readily obtained from Gc protein which may be purified from the plasma of retired human blood in large volume, according to known purification procedures.

The human Gc protein phenotypes Gc1 and Gc2, and the Gc1 subtypes Gc1f and Gc1s, are expressed inter alia as differences in the oligosaccharides attached to the polypeptide portion of the Gc molecule. The novel macrophage activating factor of the invention may be efficiently produced from Gc1f or Gc1s protein by incubation with a combination of β-galactosidase and sialidase, or a combination of β-galactosidase and α-mannosidase, respectively. If the Gc1s comprises at least in part the Gc1s variant, Gc1s*, which contains sialic acid (N-acetyl-D-neuramic acid, or "NeuNAc") in lieu of α-mannose, the mixture of enzymes utilized to treat the Gc1s/Gc1s* mixture advantageously also includes sialidase. Treatment of the Gc2 protein with β-galactosidase alone efficiently yields the macrophage activating factor. The in vitro conversion of Gc protein to macrophage activating factor by the action of commercially available enzymes is so efficient that an extremely high activity of macrophage activating factor is obtained.

Due to its genetic polymorphism, Gc protein obtained from pooled retired human blood will likely contain all three principal Gc types. Complete conversion of a mixture of Gc proteins to macrophage activating factor may thus most expeditiously be achieved by treatment with all three enzymes, as an enzyme mixture.

The molecules of the Gc1 and the Gc2 phenotypes are believed to differ by four amino acids at positions 152, 311, 416 and 420, as reported in the literature and reproduced in FIGS. 1A–1B and 2A–2B. The differences are as follows:

|  | 152 | 311 | 416 | 420 |
|---|---|---|---|---|
| Gc1 | Glu | Arg | Glu | Thr |
| Gc2 | Gly | Glu | Asp | Lys |

All three principal Gc types—Gc1s, Gc1f and Gc2—differ in the nature of the appended oligosaccharide, although it is believed that most Gc2 molecules are unglyosylated. Only the glycosylated form of Gc2 is a precursor for macrophage activating factor according to the process described herein. Incubation of each of Gc1f, Gc1s and Gc2 molecules with galactose-specific lectin beads absorbed all three macrophage activator precursor types. Thus, the outer oligosaccharide moiety of each of the three principal human Gc types is believed to be galactose.

Gc2 protein treated with β-galactosidase alone efficiently activates macrophages. Therefore, removal of galactose from Gc2 protein, to the extent the molecule is present in its glycosylated form, results in the formation of the macrophage activating factor. On the other hand, two glycosidases are required to convert the Gc1 proteins to macrophage activating factor. Conversion of Gc1f to the macrophage activity factor requires incubation with the combination of β-galactosidase and sialidase. Conversion of Gc1s requires β-galactosidase and α-mannosidase (or β-galactosidase and sialidase, in the case of Gc1s*).

The innermost sugar of the oligosaccharide moiety of Gc1 protein is N-acetylgalactosamine (Coppenhaver et al., *Arch Biochem. Biophys.* 226, 218–223, 1983). Treatment of Gc1 protein with endo-N-acetylglucosaminidase, which results in the cleavage of the N-acetylgalactosamine, results in a molecule which cannot be then converted to macrophage activating factor.

It is believed that the Gc protein phenotypes and subtypes are characterized as glycoproteins having the following oligosaccharide structures linked to an amino acid residue of the protein portion of the molecule:

| | | |
|---|---|---|
| Gc1f, Gc1s* | Gal—GalNac— | |
| | NeuNAc | |
| Gc1s | Gal—GalNAc— | |
| | αMan | |
| Gc2 | Gal—GalNAc— | |

Without wishing to be bound by any theory, it is believed that the above glycosylation occurs at the specific protein portion of the Gc glycoprotein through a threonine residue occurring at amino acid position 420 (Gc1 phenotype) or through a threonine residue occurring at neighboring amino acid position 418 (Gc2 phenotype), thus forming the O-glycosidic linkage GalNAcα(1→0)-Thr. Thus, without wishing to be bound by any theory, the novel macrophage activating factor is believed to comprise a protein in substantially pure form having substantially the amino acid sequence of human group specific component, and a terminal N-acetylgalactosamine group linked to an amino acid residue, most likely threonine 420 and/or 418.

Further without wishing to be bound by any theory, it is believed that Gc types 1f and 1s* have the same oligosaccharide moiety, but differ in amino acid sequence. The site of the yet unknown variation in amino acid sequence is postulated to be present in the vicinity of amino acid position 420.

Human Gc protein of high purity for use in the process of the invention is most readily prepared by 25-hydroxyvitamin $D_3$-Sepharose® affinity chromatography from retired blood according to the procedure of Link et al., *Anal. Buiochem.* 157, 262 (1986), the entire disclosure of which is incorporated herein by reference. The Gc protein may also be purified by actin-agarose affinity chromatography according to the procedure of Haddad et al., *Biochem. J.* 218, 805 (1984), which takes advantage of the binding specificity of Gc protein for actin. The entire disclosure of Haddad et al., is incorporated herein by reference. Other methods of obtaining Gc protein in high purity are reported in the literature.

The glycosidases utilized in the practice of the invention are well known and commercially available. Galactosidase, (β-D-galactosidase galactohydrolase, Ec 3.2.1.23) is obtained from *Escherichia coli.* β-Galactosidase is available, for example, from Boehringer Mannheim Biochemicals, Indianapolis, Ind., cat. no. 634395.

α-Mannosidase (α-D-mannoside mannohydrolase, EC 3.2.1.24) is obtained from the jack bean (*Canavalia ensiformis*). It is available, for example, from Boehringer Mannheim Biochemicals, cat. no. 269611.

Sialidase, also known as "neuraminidase" (acylneuraminyl hydrolase EC 3.2.1.18), is obtained from *Clostridium perfringens, Vibrio cholerae* or *Arthrobacter ureafaciens.* All three forms of sialidase are available from Boehringer Mannheim Biochemicals, cat. nos. 107590, 1080725 and 269611.

Gc protein is readily converted to the macrophage activating factor by contact with a hydrolytic-effective amount of one or more of the above glycosidases. Any amount of enzyme sufficient to achieve substantially complete conversion of Gc protein to macrophage activating factor may be utilized. About 0.1 units (1 unit being the amount of enzyme which catalyzes 1 μmole of substrate in 1 minute) of each enzyme per 2.6 μg of Gc protein is more than sufficient for this purpose. Preferably, an excess of the amount of enzyme actually necessary to convert the glycoprotein to macrophage activating factor is utilized to insure complete conversion.

The Gc protein and enzymes may be contacted in, for example, phosphate buffer or acetate buffer. A phosphate buffer is preferred (pH 5.5). Other media known to those skilled in the art for conducting enzymatic reactions may be substituted.

The reaction may be carried out at any temperature suitable for conducting enzymatic reactions. Typically, the temperature may vary from 25° C. to 37° C., with about 37° C. being preferred. The substrate and enzyme(s) are allowed to incubate in the reaction media until substantial conversion of the Gc protein to macrophage activating factor is achieved. While it may be appreciated that the actual incubation times employed may depend upon several factors such as the concentration of the reactants, the reaction temperature, and the like, a reaction time of about 30 minutes at 37° C. is generally sufficient to obtain complete conversion of Gc protein to macrophage activating factor.

Conversion of Gc protein to macrophage activating factor may be conducted in any vessel suitable for enzymatic reactions. It is preferred that sialidase is utilized in insoluble form, e.g., attached to beaded agarose (Sigma Chemical Co., cat. no. N-4483), to avoid contamination of the resulting macrophage activating factor with sialidase fragments of similar molecular weight. The macrophage activating factor may be produced by adding the appropriate enzyme(s) to Gc protein in a liquid medium, followed by subsequent filtration of the liquid to recover the macrophage activating factor. For example, the enzyme-Gc protein reaction mixture may be passed through a sterilized 100 kDa cut off filter (e.g. Amicon YM 100) to remove the immobilized sialidase, β-galactosidase (MW=540 kDa) and α-mannosidase (MW=190 kDa). The filtrate contains substantially pure macrophage activating factor of high activity.

Where the conversion of large quantities of Gc protein to macrophage activating factor is desired, all enzymes are most advantageously contained in the solid phase. β-Galactosidase, and sialidase or α-mannosidase, most preferably a mixture of all three enzymes, is affixed to, e.g., agarose beads with a suitable coupling agent such as cyanogen bromide. Methods for attaching enzymes to solid supports are known to those skilled in the art. Conversion of Gc protein to macrophage activating factor by means of incubation with immobilized enzymes is preferred, as the subsequent step of separating the macrophage activating factor from the enzyme mixture is obviated.

Regardless of whether immobilized or liquid phase enzyme is utilized, it is desired to pass the product mixture through an ultrafilter, preferably a filter having a pore size no larger than about 0.45µ, to provide an aseptic preparation of macrophage activating factor.

Without wishing to be bound by any theory, it is believed that B-cells possess the function corresponding to β-galactosidase, and that T-cells carry the functions corresponding to sialidase and α-mannosidase. It is believed that Gc protein is modified in vivo in an ordered sequence by the membranous enzymes of B and T lymphocytes to yield macrophage activating factor.

Activation of macrophages, which is characterized by their consequent enhanced phagocytic activity, is the first major step in a host's immune defense mechanism. Macrophage activation requires B and T lymphocyte functions, which modify Gc protein in a step-wise fashion, to yield the novel macrophage activating factor. Since the glycosidases used for in vitro conversion of Gc protein to macrophage activating factor according to the present invention correspond to the B- and the T-cell function required for production of macrophage activating factor, the in vitro enzymatic generation of the macrophage activating factor bypasses the functions of B- and T-cells. Thus, in vitro enzymatic-generated macrophage activating factor may be used for the therapy of immuno-deficient diseases, cancer and other disease conditions characterized by the immunocompromise of the afflicted individual. Moreover, since the herein described in vitro-generated macrophage activating factor is of human origin, side effects, such as immunogenicity, are believed to be minimal.

To minimize any possible immunologic reaction from administration of the macrophage activating factor, it is preferred that individuals of phenotype Gc1 would receive only Gc1-derived macrophage activating factor. Similarly, the risk of immunologic reaction in Gc2 individuals would be minimized by administering only Gc2-derived macrophage activating factor.

The novel macrophage activating factor is also believed useful in the treatment of disorders characterized by a disruption or loss of B- or T-cell function. Such disorders may be characterized by a lack of macrophage activation. Addition of exogenous macrophage activating factor of the invention will result in the restoration of macrophage activity, even in the absence of complete B- or T-cell function.

The macrophage activating factor may be administered to an individual to induce macrophage activation, either alone or in combination with other therapies. The amount of macrophage activating factor administered depends on a variety of factors, including the potency of the agent, the duration and degree of macrophage activation sought, the size and weight of the subject, the nature of the underlying affliction, and the like. Generally, administration of as little as about 0.5 ng of factor per kg of the subject's body weight will result in substantial macrophage activation. According to one treatment, a human subject may receive as little as about 30-35 ng of macrophage activating factor every three to five days to maintain a significant level of macrophage activation.

The macrophage activating factor may be administered by any convenient means which will result in delivery to the circulation of an amount of the factor sufficient to induce substantial macrophage activation. For example, it may be delivered by intravenous or intramuscular injection. Intravenous administration is presently preferred as the route of administration.

The macrophage activating factor may be taken up in pharmaceutically acceptable carriers, particularly those carriers suitable for delivery of proteinaceous pharmaceuticals. The factor is soluble in water or saline solution. Thus, the preferred formulation for pharmacological use comprises a saline solution of the agent. The formulation may optionally contain other agents, such as adjuvants to maintain osmotic balance. For example, a typical carrier for injection may comprise an aqueous solution of 0.9% NaCl or phosphate buffered saline (a 0.9% NaCl aqueous solution containing 0.01M sodium phosphate, ≈pH 7.0).

The invention is illustrated by the following non-limiting examples.

EXAMPLE 1

A. Conversion of Gc Protein to Macrophage Activating Factor

Gc protein (2.6 µg; Gc1 or Gc2) in 1 ml of phosphate-buffered saline (PBS-Mg) containing 0.01M sodium phosphate, 0.9% NaCl and 1 mM $MgSO_4$ was treated with 2 µl of PBS-Mg containing 0.1 U of the following enzymes or enzyme combinations.

Gc1f/Gc1s* conversion: sialidase (Boehringer Mannheim Biochemicals, cat. no. 107590) and β-galactosidase (Boehringer, cat. no. 634395);

Gc1s conversion: α-mannosidase (Boehringer, cat. no. 107379) and β-galactosidase;

Gc2 conversion: β-galactosidase only.

The respective enzyme-Gc protein mixtures were incubated in microcentrifuge tubes for thirty minutes at 37° C. The reaction mixture containing the treated Gc protein was then diluted $10^{-4}$, $10^{-5}$ or $10^{-6}$ in 0.1% egg albumin (EA) medium, for the following assay.

B. In Vitro Assay of Macrophage Activating Factor

1. Preparation of Macrophage Tissue Culture

Peritoneal cells were collected by injecting 5 ml of phosphate buffered saline, containing 0.01M sodium phosphate, 0.9% NaCl and 5 units/ml heparin into the peritoneal cavity of BALB/c mice. Peritoneal cells were removed and washed by low speed centrifugation and suspended in a tissue culture medium RPMI 1640 supplemented with 0.1% egg albumin (EA) medium at a concentration of $1-2\times10^6$ cells/ml. 1 ml aliquots of the cell suspension were layered onto 12 mm coverglasses which had been placed in the 16 mm diameter wells of tissue culture plates (Costar, Cambridge, Mass.). The plates were incubated at 37° C. in a 5% $CO_2$ incubator for 30 minutes to allow macrophage adherence to the coverglass. The coverglasses were removed, immersed with gentle agitation in RPMI medium to dislodge non-adherent B and T cells, and placed in fresh tissue culture wells containing EA-medium.

2. Preparation of Sheet Erythrocyte/Rabbit Anti-erythrocyte IgG Conjugates

Washed sheep erythrocytes were coated with subagglutinating dilutions of the purified IgG fraction of rabbit anti-sheep erythrocyte antibodies. A 0.5% suspension of rabbit IgG-coated sheep erythrocytes in RPMI 1640 medium was prepared for use in the following phagocytosis assay.

3. Phagocytosis Assay 1 ml aliquots of the diluted reaction mixture from A., above, were layered onto the macrophage-coated coverglasses from B.1., above, and incubated for 2 hours in a 5% $CO_2$ incubator at 37° C. The culture media was then removed and 0.5 ml of the 0.5% erythrocyte-IgG conjugate suspension were added to the macrophage-coated coverglasses and incubated for 1 hour at 37° C. The coverglasses were then washed in a hypotonic solution (1/5 diluted phosphate buffered saline in water) to lyse non-ingested erythrocytes. The macrophages with ingested erythrocytes were counted. The average number of erythrocytes ingested per macrophage was also determined. Macrophage phagocytic activity was calculated as an "Ingestion index" (the percentage of macrophages which ingested erythrocytes × the average number of erythrocytes ingested per macrophage). The data is set forth in Table 1 (Gc1) and Table 2 (Gc2).

TABLE 1

| Dilution of Glycosidase-Treated Gc1[1] Protein | Ingestion Index | | |
|---|---|---|---|
| | Gc1 untreated control | Gc1 treated with β-galactosidase and sialidase | Gc1 treated with β-galactosidase and α-mannosidase |
| $10^{-4}$ | 75 ± 10 | 352 ± 15 | 295 ± 11 |
| $10^{-5}$ | 82 ± 11 | 286 ± 11 | 210 ± 8 |
| $10^{-6}$ | 79 ± 8 | 122 ± 7 | 109 ± 13 |

[1]Mixture of Gc1f and Gc1s

TABLE 2

| Dilution of Glycosidase-Treated Gc2 Protein | Ingestion Index | |
|---|---|---|
| | Gc2 untreated control | Gc2 treated with β-galactosidase |
| $10^{-4}$ | 65 ± 13 | 325 ± 16 |
| $10^{-5}$ | 69 ± 11 | 208 ± 17 |
| $10^{-6}$ | 71 ± 20 | 116 ± 5 |

EXAMPLE 2

A. Conversion of Gc Protein to Macrophage Activating Factor with Immobilized Enzyme

1. Preparation of Immobilized Enzymes 100 mg of CNBr-activated agarose (Sepharose ® 4B) was washed with 1 mM HCl and suspended in coupling buffer (300 μl) containing $NaHCO_3$ buffer (0.1M, pH 8.3) and NaCl (0.5M). β-Galactosidase, α-mannosidase and sialidase (2 U each enzyme) were mixed in 600 μl of the coupling buffer and incubated at room temperature for 2 hours in an end-over-end mixer. Remaining active groups in the agarose were blocked by incubation with 0.2M glycine in coupling buffer for 2 hours at room temperature. The agarose-immobilized enzyme was washed with coupling buffer to remove unabsorbed protein and glycine, followed by washing with acetate buffer (0.1M, pH 4) containing NaCl (0.5M), and additional coupling buffer. The agarose-immobilized enzyme preparations were stored at 4° C.

2. Conversion of Gc Protein to Macrophage Activating Factor

Gc protein (2.6 μg; Gc1, Gc2, or mixture thereof) in 1 ml of PBS-Mg (pH 5.5) was combined with a mixture of the above-prepared agarose-immobilized enzymes (2 units each enzyme) in 1 ml of PBS-Mg (pH 5.5). The reaction mixtures were incubated in 5 ml plastic tubes at 37° C. in an end-over-end mixer for 30 minutes. The reaction mixtures were thereafter spun with a table-top centrifuge at 2,000 rpm for 15 minutes. The supernatant of each reaction mixture was collected, filtered through a sterilized 0.45μ pore size filter (type HA, Millipore Company, Bedford, Mass.), and diluted.

B. In Vivo Assay of Macrophage Activating Factor

The enzymatically-modified Gc protein (40, 10, 4 and 1 picogram samples) were administered intramuscularly to BALB/c mice weighing ~20 grams. At 18 hours post-administration, peritoneal cells were collected and placed on 12 mm coverglasses in the 16 mm wells of tissue culture plates. The plates were incubated at 37° C. for 30 minutes to allow adherence of macrophages. The coverglasses were washed in RPMI 1640 medium to dislodge non-adherent cells, and then placed in new wells. Rabbit IgG-coated sheep erythrocytes as prepared in Example 1B.2. were layered onto the coverglass, and a phagocytosis assay was performed as in Example 1B.3. The results are set forth in Table 3:

TABLE 3

| Dosage of enzymatically modified Gc protein (picogram/mouse) | Ingestion Index | | | |
|---|---|---|---|---|
| | Untreated Control | | Glycosidase-treated | |
| | Gc1 | Gc1 + Gc2 | Gc1 | Gc1 + Gc2 |
| 40 | 57 ± 16 | 59 ± 7 | 322 ± 19 | 314 ± 11 |
| 10 | 55 ± 10 | 63 ± 13 | 353 ± 16 | 332 ± 14 |
| 4 | 51 ± 12 | 45 ± 8 | 163 ± 18 | 152 ± 13 |
| 1 | 63 ± 18 | 56 ± 9 | 114 ± 3 | 106 ± 5 |

The present invention may be embodied in other specific forms without departing from the spirit or essential attributes thereof and, accordingly, reference should be made to the appended claims, rather than to the foregoing specification, as indicating the scope of the invention.

I claim:

1. A process for producing a macrophage activating factor comprising contacting glycosylated human group-specific component in vitro with
   β-galactosidase, or
   β-galactosidase in combination with sialidase, α-mannosidase, or a mixture thereof,
   and obtaining the macrophage activating factor.

2. A process according to claim 1 wherein the group-specific component is of phenotype Gc1, subtype Gc1f, which component is contacted with β-galactosidase and sialidase.

3. A process according to claim 1 wherein the group-specific component is of phenotype Gc1, subtype Gc1s, which component is contacted with β-galactosidase and α-mannosidase.

4. A process according to claim 3 wherein the group-specific component is of phenotype Gc1, variant Gc1s*, which component is contacted with β-galactosidase and sialidase.

5. A process according to claim 1 wherein the group-specific component is of phenotype Gc2, which component is contacted with β-galactosidase.

6. A process according to claim 1 wherein group-specific component comprising a mixture of components of types Gc1f, Gc1s and Gc2 is contacted with a mixture of glycosidases comprising β-galactosidase, sialidase and α-mannosidase.

7. A process according to claim 1 wherein the enzyme or enzymes is immobilized on a solid support.

8. A process according to claim 7 wherein the solid support comprises agarose.

9. A macrophage activating factor prepared by the process of claim 1.

10. A macrophage activating factor prepared by the process of claim 2.

11. A macrophage activating factor prepared by the process of claim 3.

12. A macrophage activating factor prepared by the process of claim 4.

13. A macrophage activating factor prepared by the process of claim 5.

14. A macrophage activating factor prepared by the process of claim 6.

15. A macrophage activating factor prepared by the process of claim 7.

16. A macrophage activating composition comprising, in combination with a pharmaceutically acceptable carrier, a macrophage activating factor formed by treating glycosylated human group-specific component in vitro with
    $\beta$-galactosidase or
    $\beta$-galactosidase in combination with sialidase $\alpha$-mannosidase, or mixtures thereof.

17. A macrophage activating composition according to claim 16 wherein the group-specific component is of phenotype Gc1, subtype Gc1f, which group-specific component is treated with $\beta$-galactosidase and sialidase.

18. A macrophage activating composition according to claim 16 wherein the group-specific component is of phenotype Gc1, subtype Gc1s, which component is treated with $\beta$-galactosidase and $\alpha$-mannosidase.

19. A macrophage activating composition according to claim 16 wherein the group-specific component is of phenotype Gc1, variant Gc1s*, which component is treated with $\beta$-galactosidase and sialidase.

20. A macrophage activating composition according to claim 16 wherein the group-specific component is of phenotype Gc2, which component is treated with $\beta$-galactosidase.

21. A macrophage activating composition according to claim 16 wherein the group-specific component comprising a mixture of components of types Gc1f, Gc1s and Gc2 is treated with a mixture of glycosidases comprising $\beta$-galactosidase, sialidase and $\alpha$-mannosidase.

22. A method for inducing macrophage activation in an individual in need thereof comprising administering to such an individual macrophage activating factor prepared by contacting glycosylated human group-specific component in vitro with
    $\beta$-galactosidase, or
    $\beta$-galactosidase in combination with sialidase, $\alpha$-mannosidase, or a mixture thereof.

* * * * *